US006969486B1

(12) United States Patent
Cooper et al.

(10) Patent No.: US 6,969,486 B1
(45) Date of Patent: Nov. 29, 2005

(54) APPARATUS AND METHOD FOR TREATING POLLUTANTS IN A GAS USING HYDROGEN PEROXIDE AND UV LIGHT

(75) Inventors: Charles David Cooper, Maitland, FL (US); Christian Anthony Clausen, Chuluota, FL (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 709 days.

(21) Appl. No.: 10/056,842

(22) Filed: Jan. 18, 2002

Related U.S. Application Data

(60) Provisional application No. 60/267,401, filed on Feb. 7, 2001.

(51) Int. Cl.[7] .................................................. A61L 2/00
(52) U.S. Cl. .............................. 422/4; 422/23; 422/24; 422/186.3; 423/210
(58) Field of Search ............................... 422/4, 23, 24, 422/186.3; 423/210

(56) References Cited

U.S. PATENT DOCUMENTS

| | | | |
|---|---|---|---|
| 4,009,252 A * | 2/1977 | Izumi et al. ................. 423/584 |
| 4,012,321 A | 3/1977 | Koubek ........................ 210/63 |
| 4,344,918 A * | 8/1982 | Takahashi ..................... 422/80 |
| 4,849,114 A | 7/1989 | Zeff et al. ..................... 210/747 |
| 5,129,212 A * | 7/1992 | Duffey et al. ................. 53/426 |
| 5,168,193 A * | 12/1992 | Hoegler ....................... 313/113 |
| 5,256,379 A * | 10/1993 | DeLoach ................. 422/186.3 |
| 5,439,595 A | 8/1995 | Downey, Jr. ................. 210/748 |
| 5,470,480 A | 11/1995 | Gray et al. ................. 210/632 |
| 5,670,122 A | 9/1997 | Zamansky et al. .......... 423/210 |
| 6,047,543 A | 4/2000 | Caren et al. .................. 60/275 |
| 6,264,899 B1 | 7/2001 | Caren et al. ............. 422/186.3 |

* cited by examiner

*Primary Examiner*—John Kim
*Assistant Examiner*—Brad Chin
(74) *Attorney, Agent, or Firm*—Randall M. Heald; Gary G. Borda; Guy Miller

(57) ABSTRACT

An apparatus for treating pollutants in a gas may include a source of hydrogen peroxide, and a treatment injector for creating and injecting dissociated hydrogen peroxide into the flow of gas. The treatment injector may further include an injector housing having an inlet, an outlet, and a hollow interior extending therebetween. The inlet may be connected in fluid communication with the source of hydrogen peroxide so that hydrogen peroxide flows through the hollow interior and toward the outlet. At least one ultraviolet (UV) lamp may be positioned within the hollow interior of the injector housing. The at least one UV lamp may dissociate the hydrogen peroxide flowing through the tube. The dissociated hydrogen peroxide may be injected into the flow of gas from the outlet for treating pollutants, such as nitrogen oxides.

32 Claims, 3 Drawing Sheets

APPARATUS AND METHOD FOR TREATING POLLUTANTS IN A GAS USING HYDROGEN PEROXIDE AND UV LIGHT

RELATED APPLICATION

This application is based upon provisional application Ser. No. 60/267,401 filed Feb. 7, 2001, the entire contents of which are incorporated herein by reference.

ORIGIN OF INVENTION

The invention described herein was made in the performance of work under a NASA contract and by an employee of the United States Government and is subject to the provisions of Public Law 96-517 (35 U.S.C. §202) and may be manufactured and used by or for the Government for governmental purposes without the payment of any royalties thereon or therefore. In accordance with 35 U.S.C. §202, the contractor elected not to retain title.

FIELD OF THE INVENTION

The present invention relates generally to the field of pollution control, and, more particularly, to reducing air pollutants in gases.

BACKGROUND OF THE INVENTION

NOx and other air pollutants, such as CO and VOCs, are often found in combustion flue gasses. Selective catalytic reduction (SCR) is often used to control NOx. In particular, cheaper and more effective technology is desired to control NOx emissions from large combustion sources (power plants, large boilers, etc.).

There has been research over the past decade on using hydrogen peroxide to oxidize NOx in flue gas to more scrubbable species. The hydrogen peroxide is injected into hot flue gas and thermally splits to form very active free radicals that attack the NOx so that downstream scrubbing can remove the species created. Unfortunately, this activation of hydrogen peroxide does not readily occur at low temperatures by itself. Thus, there is a desire for technology that may also be effective even at relatively low-temperatures.

Attempts have been made to remove air pollutants from flue gasses, and, in some cases, at relatively low temperatures. For example, U.S. Pat. No. 5,670,122 to Zamansky et al. discloses a method for removing air pollutants from combustion flue gases. The method comprises adding hydrogen peroxide and/or methanol to a combustion flue gas that is between 377° C. and 827° C. The hydrogen peroxide and/or methanol react with the air pollutants in the flue gas and remove nitric oxide, sulfur trioxide, light hydrocarbons, carbon monoxide, and trace amounts of mercury from the combustion flue gas.

Other technologies use ultraviolet light to dissociate hydrogen peroxide for greater performance. For example, one approach places the UV light in the gas flow tube which carries the flue gas. Alternately, the UV light is delivered by a UV lamp in a large (dilute) liquid container within a separate reactor vessel. Prior research and practice used ordinary injection nozzles for the hydrogen peroxide that were separate from the UV light source.

Attempts have been made to improve the efficiency of removing air pollutants when using hydrogen peroxide and UV light. For example, U.S. Pat. No. 5,256,379 to Deloach discloses an apparatus for removing hydrocarbon contaminants from an air stream that flows through a chamber. UV light passes through the chamber and irradiates the hydrogen peroxide. The UV light source is located outside the chamber that the hydrogen peroxide passes through. The effect is that the hydrogen peroxide does not efficiently absorb all of the UV light because not all of the UV light passes through the chamber.

Moreover, prior technology is often limited because there are competing reactions involving the UV light, it is difficult to keep the UV lamps cooled, and there is a possibility of UV leakage out of the reactor. Thus, there is a need for technology that more efficiently irradiates hydrogen peroxide to be subsequently used for removing air pollutants from gases, such as flue gasses from stationary sources.

SUMMARY OF THE INVENTION

In view of the foregoing background, it is therefore an object of the invention to provide a method and apparatus for efficiently creating and injecting dissociated hydrogen peroxide into gases, such as flue gases, to thereby treat pollutants, such as NOx, for example.

This and other objects, features and advantages in accordance with the present invention are provided by an apparatus for treating pollutants in a gas that includes at least one UV lamp within a treatment injector housing through which the hydrogen peroxide passes. More particularly, the overall treatment apparatus may include a gas flow tube that carries a flow of gas, such as flue gas. The treatment injector cooperates with a source of hydrogen peroxide for creating and injecting dissociated hydrogen peroxide into the flow of gas. By activating the hydrogen peroxide with UV light and efficiently delivering the activated hydrogen peroxide to the gas, greater pollutant treatment efficiency may be obtained, especially at lower temperatures.

The treatment injector may further comprise an injector housing having an inlet, an outlet, and a hollow interior extending between the inlet and outlet. The inlet may be connected in fluid communication with the source of hydrogen peroxide so that hydrogen peroxide flows through the hollow interior and toward the outlet.

At least one UV lamp may be positioned within the hollow interior of the injector housing. The UV lamp may dissociate the hydrogen peroxide flowing through the injector housing. The dissociated hydrogen peroxide may be injected into the flow of gas from the outlet for treating pollutants in the flow of gas. For example, the apparatus may be for reducing nitrogen oxides in flue gas from a stationary source.

The apparatus may further comprise a scrubber connected to the gas flow tube downstream from the treatment injector. The scrubber may remove reaction products of the pollutants with the dissociated hydrogen peroxide.

Additionally, the apparatus may comprise an air source connected in fluid communication with the inlet of the injector housing. A heater may also be provided to heat the air, and, thus, heat the hydrogen peroxide within the injector housing.

The outlet of the treatment injector may be connected in fluid communication with an opening in the sidewall of the gas flow tube. In one class of embodiments, the injector housing may have a generally tubular shape that extends through the opening in the sidewall of the gas flow tube. The UV lamp may have an elongate shape and may be oriented generally parallel to the tubular shape of the injector housing. In another class of embodiments, the injector housing is external to the gas flow tube. The UV lamp may have an elongate shape and may be oriented transverse to the tubular shape of the injector housing.

The treatment injector may comprise a UV reflective coating on the interior of the injector housing. Boric acid may be used as a coating applied on the interior of the injector housing to reduce or prevent undesired decomposition of the hydrogen peroxide on the walls of the injector housing. A cooling fan may also be associated with the UV lamp.

Another aspect of the invention relates to a method for treating pollutants in a flow of gas carried by a gas flow tube and using a hydrogen peroxide source. More particularly, the method may comprise coupling a treatment injector between the hydrogen peroxide source and the gas flow tube. The treatment injector may comprise an injector housing having an inlet, an outlet and a hollow interior extending therebetween. The inlet may be connected in fluid communication with the source of hydrogen peroxide. The treatment injector may further comprise at least one UV lamp positioned within the hollow interior of the injector housing.

Furthermore, the method may include flowing hydrogen peroxide through the hollow interior of the injector housing and toward the outlet while operating the at least one UV lamp to dissociate the hydrogen peroxide. Accordingly, the dissociated hydrogen peroxide is injected into the flow of gas from the outlet for treating the pollutants.

DETAILED DESCRIPTION OF THE PREFERRED EMBODIMENTS

The present invention will now be described more fully hereinafter with reference to the accompanying drawings, in which preferred embodiments of the invention are shown. However, this invention may be embodied in many different forms and should not be construed as limited to the embodiments set forth herein. Rather, these embodiments are provided so that this disclosure will be thorough and complete and will fully convey the scope of the invention to those skilled in the art. Like numbers refer to like elements throughout.

Figure 1:
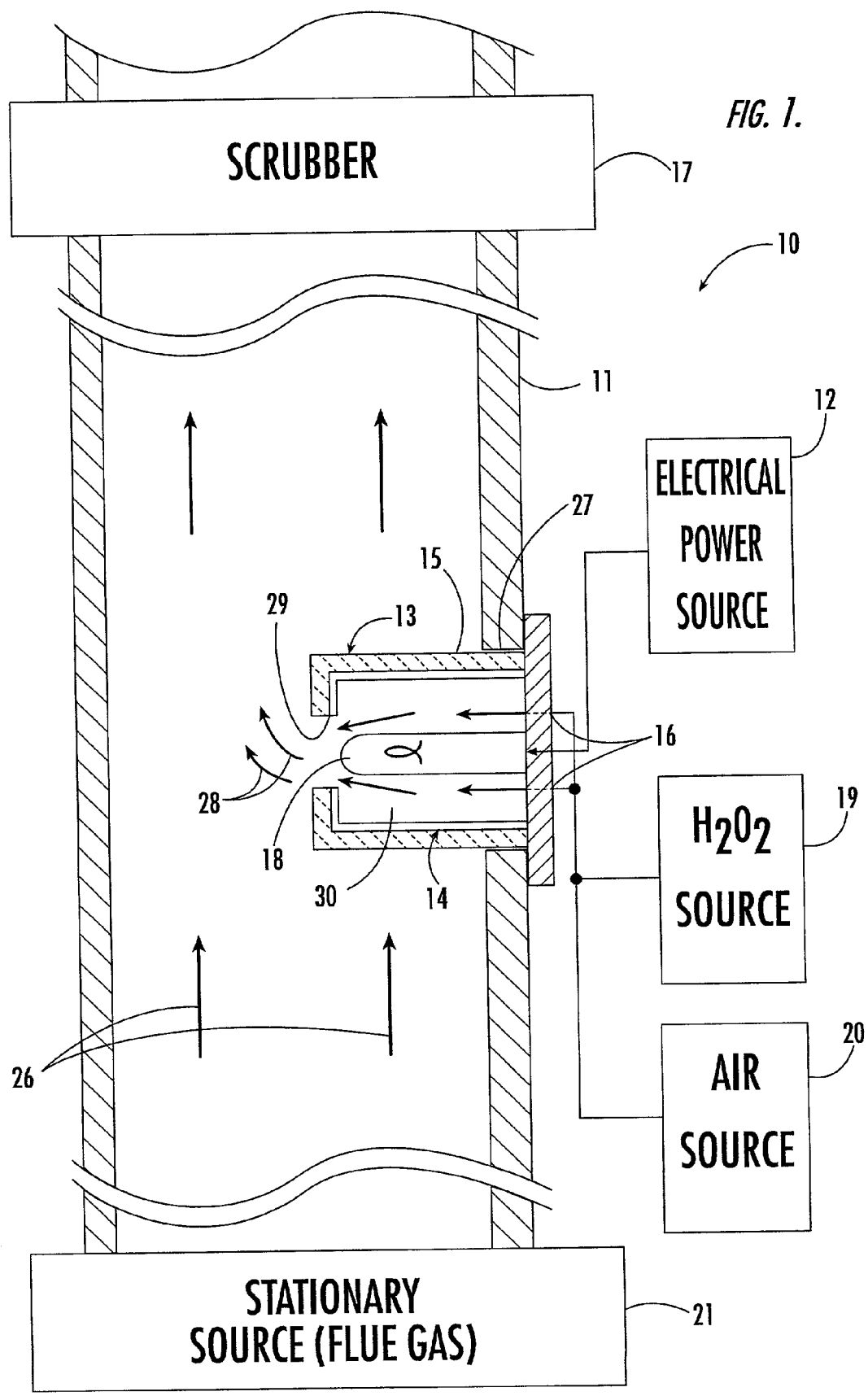
FIG. 1 is a schematic diagram of a first embodiment of the apparatus in accordance with the invention.

Referring to FIG. 1, a first embodiment of the apparatus 10 for treating a gas including pollutants is now described. In the illustrated embodiment, the apparatus 10 includes a gas flow tube 11 having a sidewall opening 27 therein. The gas flow tube 11 carries a flow of gas illustrated by the arrows labeled 26. For example, the gas 26 may be a flue gas from a stationary source 21, such as a power plant, industrial boiler, or other similar source as will be appreciated by those skilled in the art. Of course, in other embodiments, the source may be mobile rather than stationary.

The apparatus 10 also includes a source of hydrogen peroxide 19. For example, the hydrogen peroxide source 19 may deliver the hydrogen peroxide as a mist or liquid as will be appreciated by those skilled in the art. A treatment injector 13 is connected to and cooperates with the source of hydrogen peroxide 19 for injecting radicals formed by the dissociation of the hydrogen peroxide and indicated by arrows labeled 28 into the flow of gas 26.

The treatment injector 13, in turn, illustratively includes an injector housing 15 having one or more inlets 16, an outlet 29, and a hollow interior 30 extending therebetween. The inlet 16 may be connected in fluid communication with the source of hydrogen peroxide 19 so that hydrogen peroxide flows through the hollow interior 30 of the injector housing 15 and toward the injector housing outlet 29. In other words, the hydrogen peroxide is at a higher pressure than the pressure of the flue gas 26 and therefore flows through the hollow interior 30 of the injector housing 15.

A UV lamp 18 is illustratively positioned within the hollow interior 30 of the injector housing 15. The UV lamp 18 is connected to the electrical power source 12 and provides UV radiation which dissociates the hydrogen peroxide flowing through the injector housing 15 to generate the radicals to thereby treat one or more pollutants in the flue gas 26 as will be appreciated by those skilled in the art. One advantage of positioning the UV lamp 18 within the hollow interior 30 of the injector housing 15 is that the flow of hydrogen peroxide also provides cooling for the lamp.

The dissociated hydrogen peroxide 28 may be discharged from the outlet 29 and into the flow of gas 26, such as for converting nitrogen oxides into compounds which can be readily removed by the downstream scrubber 17, for example. Other pollutants that may be similarly treated include, without limitation, CO and various VOCs, for example. Further details regarding the chemistry for removal of nitrogen oxides, for example, such as emitted from a stationary source 21 and using hydrogen peroxide radicals will be appreciated by those skilled in the art. A further discussion may be found in copending U.S. patent application Ser. No. 09/698,607, entitled ?Air Pollution Control Method and Apparatus For Removal of Nitrogen Oxides From Station Combustion Sources, filed on Oct. 27, 2000, and assigned to the assignee of the present invention. The entire contents of this patent application are incorporated herein by reference.

The apparatus 10 also illustratively includes an air source 20, connected in fluid communication with the inlet 16 of the injector housing 15. The air source 20 may be optionally used to provide the desired positive pressure to cause the flow of dissociated hydrogen peroxide 28 from the outlet 29 as will be appreciated by those skilled in the art. Of course the air flow may also provide cooling for the UV lamp 18.

In the illustrated embodiment, the injector housing 15 is positioned to extend into the sidewall opening 27 of the gas flow tube 11. The injector housing 15, may have a generally tubular shape, for example, although other shapes are also contemplated by the invention. The UV 18 lamp also illustratively has an elongate shape and is oriented generally parallel to the tubular shape of the injector housing 15. Other similar UV lamp 18 orientations known to one of ordinary skill in the art are also possible. In addition, multiple such lamps 18 may be positioned within the hollow interior 30 of the injector housing 15 as will be described in greater detail below.

The injector housing 15 may comprise metal or a ceramic material, for example. In addition, at least one coating 14 may be provided on the interior of the injector housing 15. The coating 14 may be a UV reflective material, for example. The coating 14 may alternately comprise boric acid to help prevent undesired decomposition of the hydrogen peroxide. Of course, other materials may also be used as a coating 14 with similar advantageous properties to boric acid, for example, as will be appreciated by those skilled in the art.

Figure 2:
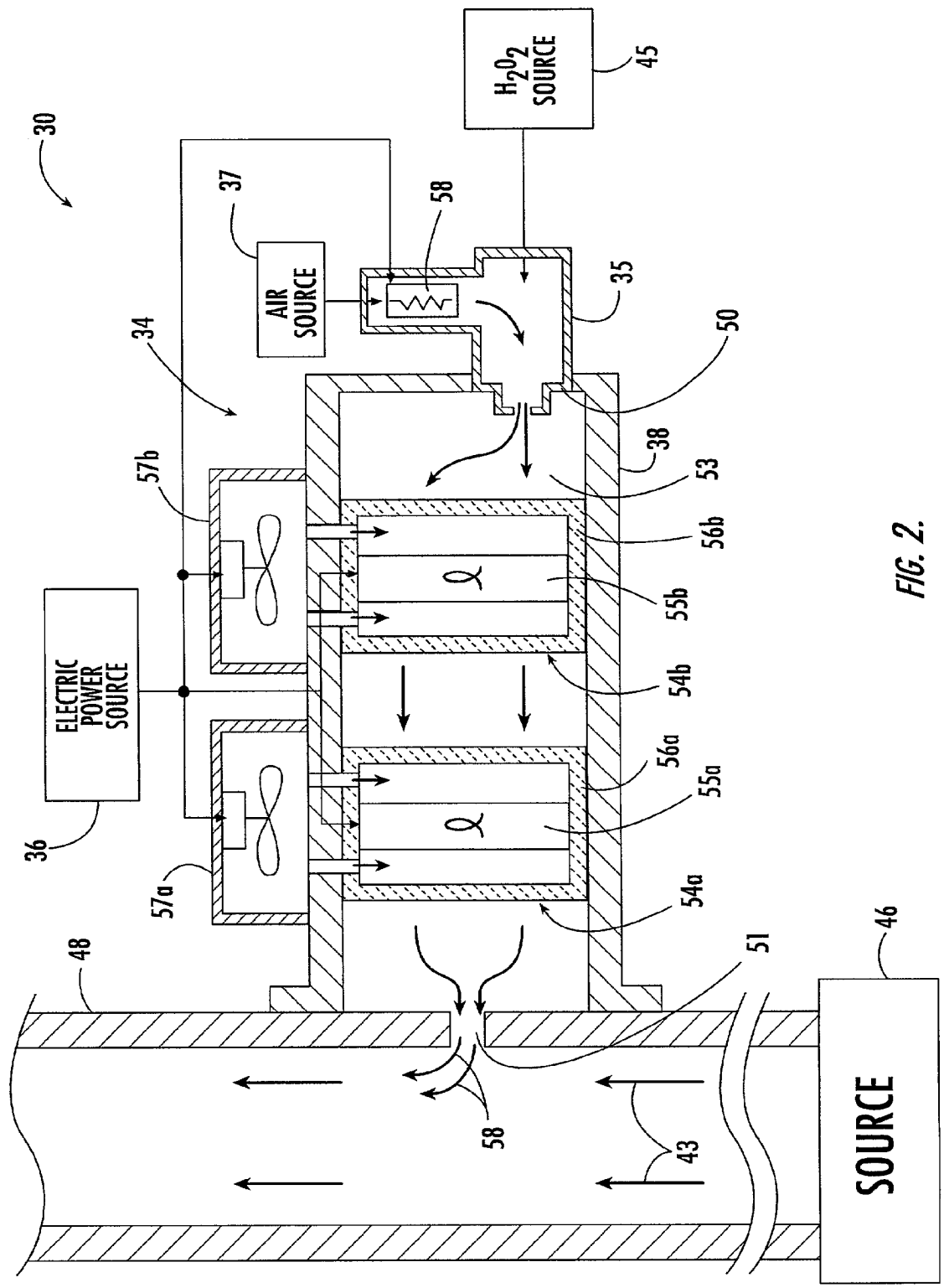
FIG. 2 is a schematic diagram of a second embodiment of the apparatus in accordance with the invention.

Turning now additionally to FIG. 2, a second embodiment of the apparatus 30 in accordance with the invention is now described. In this embodiment, the treatment injector 34 and its housing 38 are completely external to the gas flow tube 48 which carries the flow of gas 43 from the source 46.

The injector housing includes an inlet 50, an outlet 51 and a hollow interior 53 extending therebetween as in the above described embodiment. The outlet 51 is coupled to the flow of gas 43 from the source 46 and through the gas flow tube 48.

In this embodiment, however, a pair of UV lamp assemblies 54a, 54b are positioned in spaced apart relation and extend transverse to the hollow interior 53 and, thus, transverse to the flow of hydrogen peroxide through the interior. Each UV lamp assembly 54a, 54b illustratively includes a respective UV lamp 55a, 55b surrounded by a respective quartz or UV transparent housing 56a, 56b. Each UV lamp assembly 54a, 54b also illustratively includes a respective optional air blower 57a, 57b for delivering a flow of cooling air into the space between the housing and lamp. The UV lamp assemblies 54a, 54b create dissociated hydrogen peroxide 58 which exits through the outlet 51 and into the flow of gas 43 being treated.

The inlet 50 is coupled to a chamber 35 which, in turn, is connected to the hydrogen peroxide source 45. An air source 37 is also coupled to the chamber 35 so that a flow of air can be controllably added to the flow of hydrogen peroxide. In addition, a heater 58 is illustratively provided in the chamber 35 to thereby heat the air, and, thus, heat the hydrogen peroxide as will be appreciated by those of skill in the art. The heater 38 is connected to an electric power source 36, as are the UV lamp assemblies 54a, 54b and blowers 57a, 57b. The heater 38 is optional and may not be needed in all embodiments as will also be appreciated by those skilled in the art.

Figure 3:
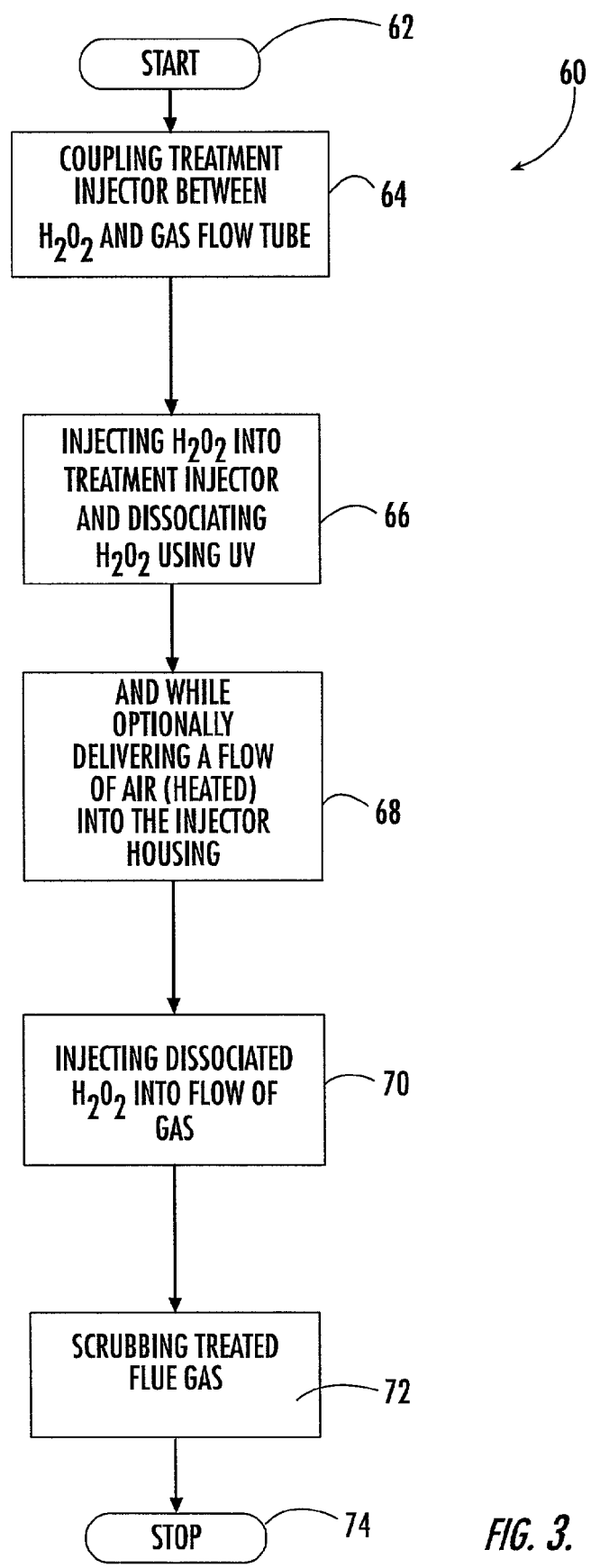
FIG. 3 is a flow chart illustrating a method in accordance with the invention.

Another aspect of the invention relates to a method for reducing pollutants in a flow of gas carried by a gas flow tube using a hydrogen peroxide source. This method is more fully explained with additional reference to the flow chart 60 of FIG. 3. From the start (Block 62), the method includes at Block 66 coupling a treatment injector 13 (FIG. 1), 34 (FIG. 2) between the hydrogen peroxide source 19, 45 and the gas flow tube 11, 48. The treatment injector 13, 34 may comprise an injector housing 15, 38 having an inlet 16, 50, an outlet 29, 51, and a hollow interior 30, 53 extending therebetween. The inlet 16, 50 may be connected in fluid communication with the source of hydrogen peroxide 19, 45. The treatment injector 13, 34 may further comprise at least one UV lamp 18, 55a, 55b positioned within the hollow interior 13, 53 of the injector housing 15, 38.

At Block 66 hydrogen peroxide is flowed through the hollow interior 30, 53 of the injector housing 15, 38 and toward the outlet 29, 51 while operating the at least one UV lamp 18, 54a, 54b to dissociate hydrogen peroxide 28, 58.

At Block 68 the method may also include delivering a flow of air, such as heated air, to the inlet 29, 51 of the injector housing 15, 38. Additionally, at Block 70 the dissociated hydrogen peroxide is injected into the flow of gas. The gas so treated may be scrubbed (Block 72) to remove reactant products formed by the dissociated hydrogen peroxide and pollutants in the flow of gas, before stopping at Block 74.

In brief summary: the apparatus and associated method use UV light to dissociate the hydrogen peroxide, and the hydrogen peroxide is closely contained adjacent to the UV lamp, thus providing cooling for the lamp, and while preheating the hydrogen peroxide. Also, containing the UV light in the treatment injector advantageously couples substantially all of the light's energy into the hydrogen peroxide so there is less wasted UV light, such as occurs in conventional treatment approaches.

The following TABLES 1–3 show test results using a prototype apparatus including the treatment injector similar to that shown in FIG. 2 and as described above. The data is broken down based upon low, medium or high temperatures. In addition, none, one or both of the UV lamps were used to generate the data as indicated. As can be readily appreciated by those skilled in the art, the treatment injector of the present invention provides more efficient conversion particularly, for low-temperature gases.

TABLE 1

Low Temperature Data

| Run | # Lamps | Temp. F. | NO Conv., % | NOx Conv., % |
|---|---|---|---|---|
| #9 | 0 | 186 | 1.1 | 0.0 |
| #8 | 0 | 186 | 1.9 | 0.0 |
| #1 | 0 | 186 | 0.0 | 0.0 |
| | | averages | 1.0 | 0.0 |
| #6 | 1 | 186 | 1.5 | 0.0 |
| #7 | 1 | 186 | 1.9 | 0.0 |
| #2 | 1 | 186 | 2.3 | 0.0 |
| | | averages | 1.9 | 0.0 |
| #5 | 2 | 186 | 1.5 | 2.2 |
| #4 | 2 | 186 | 1.9 | 2.2 |
| #3 | 2 | 186 | 4.1 | 2.2 |
| | | averages | 2.5 | 2.2 |

TABLE 2

Medium Temperature Data

| Run | # Lamps | Temp. F. | NO Conv., % | NOx Conv., % |
|---|---|---|---|---|
| #10 | 0 | 320 | 0.0 | 0.0 |
| #9 | 0 | 320 | 0.0 | 0.0 |
| #8 | 0 | 360 | 0.0 | 0.0 |
| #9 | 0 | 360 | 0.0 | 0.0 |
| #11 | 0 | 320 | 0.0 | 0.0 |
| #8 | 0 | 320 | 0.0 | 0.0 |
| #1 | 0 | 360 | 1.2 | 0.0 |
| | | averages | 0.2 | 0.0 |
| #1 | 1 | 320 | 1.7 | 0.0 |
| #6 | 1 | 320 | 5.3 | 3.4 |
| #7 | 1 | 360 | 6.1 | 2.7 |
| #6 | 1 | 360 | 15.4 | 10.7 |
| #12 | 1 | 320 | 4.8 | 2.3 |
| #2 | 1 | 320 | 6.1 | 1.5 |
| #7 | 1 | 320 | 5.7 | 0.0 |
| #2 | 1 | 360 | 6.4 | 1.9 |
| | | averages | 6.5 | 2.8 |
| #5 | 2 | 320 | 5.9 | 1.6 |
| #4 | 2 | 360 | 5.1 | 1.0 |
| #5 | 2 | 360 | 11.1 | 5.7 |
| #3 | 2 | 320 | 9.5 | 0.0 |
| #4 | 2 | 320 | 8.0 | 2.8 |
| #3 | 2 | 360 | 9.5 | 3.5 |
| | | averages | 8.2 | 2.4 |

TABLE 3

High Temperature Data

| Run | Lamps | Temp. F. | NO Conv., % | NOx Conv., % |
|---|---|---|---|---|
| #5 | 0 | 580 | 32.2 | 14.1 |
| #6 | 0 | 580 | 35.6 | 16.7 |
|  |  | averages | 33.9 | 15.4 |
| #1 | 1 | 580 | 32.7 | 15.6 |
| #2 | 1 | 580 | 52.5 | 25.2 |
|  |  | averages | 42.6 | 20.4 |
| #4 | 2 | 580 | 46.4 | 20.4 |
| #3 | 2 | 580 | 64.3 | 32.3 |
|  |  | averages | 55.4 | 26.5 |

Many modifications and other embodiments of the invention will come to the mind of one skilled in the art having the benefit of the teachings presented in the foregoing descriptions and the associated drawings. Therefore, it is to be understood that the invention is not limited to the specific embodiments disclosed, and that the modifications and embodiments are intended to be included within the scope of the depending claims.

That which is claimed is:

1. An apparatus for treating pollutants in a gas comprising:
    a gas flow tube carrying a flow of gas to be treated comprising a sidewall having an opening therein;
    a source of hydrogen peroxide;
    a treatment injector connected to the opening in the sidewall of said gas flow tube for creating and injecting dissociated hydrogen peroxide into the flow of gas to be treated, said treatment injector comprising
    an injector housing having an inlet, an outlet and a hollow interior extending therebetween, the inlet being connected in fluid communication with said source of hydrogen peroxide so that hydrogen peroxide flows through the hollow interior and toward the outlet, and
    at least one ultraviolet (UV) lamp positioned within the hollow interior of said injector housing for dissociating hydrogen peroxide flowing therethrough so that the dissociated hydrogen peroxide is injected into the flow of gas from the outlet for treating pollutants.

2. An apparatus according to claim 1 wherein the pollutants include nitrogen oxides; and further comprising a scrubber connected to said gas flow tube downstream from said treatment injector for removing reaction products of nitrogen oxides with the dissociated hydrogen peroxide.

3. An apparatus according to claim 1 further comprising an air source connected in fluid communication with the inlet of said injector housing.

4. An apparatus according to claim 1 further comprising a heater carried by said injector housing.

5. An apparatus according to claim 1 wherein the outlet is connected in fluid communication with the opening in the sidewall of said gas flow tube.

6. An apparatus according to claim 1 wherein said injector housing extends through the opening in the sidewall of said gas flow tube.

7. An apparatus according to claim 1 wherein said injector housing has a generally tubular shape.

8. An apparatus according to claim 7 wherein said at least one UV lamp has an elongate shape and is oriented generally parallel to the tubular shape of said injector housing.

9. An apparatus according to claim 7 wherein said at least one UV lamp has an elongate shape and is oriented transverse to the tubular shape of said injector housing.

10. An apparatus according to claim 1 further comprising a UV reflective coating on an interior of said injector housing.

11. An apparatus according to claim 1 further comprising a boric acid coating on an interior of said injector housing.

12. An apparatus according to claim 1 further comprising at least one cooling fan associated with said at least one UV lamp.

13. An apparatus according to claim 1 wherein the flow of gas to be treated comprises a flue gas.

14. An apparatus according to claim 1 wherein the flow of gas to be treated is from a stationary source.

15. An apparatus for treating pollutants in a flue gas from a stationary source comprising:
    a gas flow tube carrying a flow of flue gas from the stationary source comprising a sidewall having an opening therein;
    a source of hydrogen peroxide; and
    a treatment injector for creating and injecting dissociated hydrogen peroxide into the flow of flue gas from the stationary source, said treatment injector comprising
    an injector housing external to said gas flow tube and having an inlet, an outlet and a hollow interior extending therebetween, the inlet being connected in fluid communication with said source of hydrogen peroxide and the outlet being connected in fluid communication with the opening in the sidewall of said gas flow tube so that hydrogen peroxide flows through the hollow interior and toward the outlet,
    at least one ultraviolet (UV) lamp positioned within the hollow interior of said injector housing for dissociating hydrogen peroxide flowing therethrough so that the dissociated hydrogen peroxide is injected into the flow of gas from the outlet for treating pollutants; and
    a scrubber connected to said gas flow tube downstream from said treatment injector for removing reaction products of pollutants with the dissociated hydrogen peroxide.

16. An apparatus according to claim 15 further comprising an air source connected in fluid communication with the inlet of said injector housing.

17. An apparatus according to claim 15 further comprising a heater carried by said housing.

18. An apparatus according to claim 15 wherein said injector housing has a generally tubular shape.

19. An apparatus according to claim 18 wherein said at least one UV lamp has an elongate shape and is oriented generally parallel to the tubular shape of said injector housing.

20. An apparatus according to claim 18 wherein said at least one UV lamp has an elongate shape and is oriented transverse to the tubular shape of said injector housing.

21. An apparatus for treating pollutants in a flue gas from a stationary source comprising:
    a gas flow tube carrying a flow of flue gas from the stationary source comprising a sidewall having an opening therein;
    a source of hydrogen peroxide; and
    a treatment injector for creating and injecting dissociated hydrogen peroxide into the flow of flue gas from the stationary source, said treatment injector comprising:
    an injector housing extending through the opening in the sidewall of said gas flow tube, said injector housing having an inlet, an outlet and a hollow interior extending therebetween, the inlet being connected in fluid communication with said source of hydrogen peroxide so that hydrogen peroxide flows through the hollow interior and toward the outlet, at least one ultraviolet (UV) lamp positioned within the hollow interior of said injector housing for dissociating hydrogen peroxide flowing therethrough so that the dissociated hydrogen peroxide is injected into the flow of gas from the outlet for treating pollutants; and a scrubber connected to said gas flow tube downstream from said treatment injector for removing reaction products of the pollutants with the dissociated hydrogen peroxide.

22. An apparatus according to claim 21 further comprising an air source connected in fluid communication with the inlet of said injector housing.

23. An apparatus according to claim 21 further comprising a heater carried by said housing.

24. An apparatus according to claim 21 wherein said injector housing has a generally tubular shape.

25. An apparatus according to claim 24 wherein said at least one UV lamp has an elongate shape and is oriented generally parallel to the tubular shape of said injector housing.

26. An apparatus according to claim 24 wherein said at least one UV lamp has an elongate shape and is oriented transverse to the tubular shape of said injector housing.

27. A method for treating pollutants in a flow of gas carried by a gas flow tube using a hydrogen peroxide source, the method comprising the steps of:

coupling a treatment injector between the hydrogen peroxide source and the gas flow tube, the treatment injector comprising an injector housing having an inlet, an outlet and a hollow interior extending therebetween, the inlet being connected in fluid communication with the source of hydrogen peroxide, the treatment injector further comprising at least one ultraviolet (UV) lamp positioned within the hollow interior of the injector housing; and flowing hydrogen peroxide through the hollow interior of the injector housing and toward the outlet while operating the at least one UV lamp to dissociate hydrogen peroxide so that dissociated hydrogen peroxide is injected into the flow of gas from the outlet for treating pollutants in the flow of gas.

28. A method according to claim 27 further comprising the step of scrubbing reaction products of pollutants with the dissociated hydrogen peroxide from the flow of gas downstream from the treatment injector.

29. A method according to claim 27 further comprising the step of delivering a flow of air to the inlet of the injector housing.

30. A method according to claim 27 further comprising the step of heating hydrogen peroxide with the injector housing.

31. A method according to claim 27 wherein the flow of gas comprises a flue gas.

32. A method according to claim 27 wherein the flow of gas is from a stationary source.

* * * * *